(12) United States Patent
Schlagheck et al.

(10) Patent No.: US 6,840,667 B2
(45) Date of Patent: Jan. 11, 2005

(54) METHOD AND APPARATUS FOR DETECTION OF DEFECTS USING THERMAL STIMULATION

(75) Inventors: Jerry Schlagheck, West Chester, OH (US); Marc Pastor, Saint Herbert (CA); Marc Levesque, Saint Augustin-de-Desmaures (CA); Alain Cournoyer, Quebec (CA)

(73) Assignee: Photon Dynamics, Inc., San Jose, CA (US)

( * ) Notice: Subject to any disclaimer, the term of this patent is extended or adjusted under 35 U.S.C. 154(b) by 0 days.

(21) Appl. No.: 10/419,709

(22) Filed: Apr. 18, 2003

(65) Prior Publication Data

US 2004/0028113 A1 Feb. 12, 2004

Related U.S. Application Data

(63) Continuation-in-part of application No. 09/986,712, filed on Nov. 9, 2001, which is a continuation-in-part of application No. 09/648,140, filed on Aug. 25, 2000.
(60) Provisional application No. 60/371,971, filed on May 10, 2002, and provisional application No. 60/254,666, filed on Dec. 12, 2000.

(51) Int. Cl.[7] .............................................. G01N 25/72
(52) U.S. Cl. ............................ 374/5; 374/124; 374/137
(58) Field of Search ........................... 374/4–7, 43, 120, 374/121, 124, 129, 137

(56) References Cited

U.S. PATENT DOCUMENTS 5,052,816 A    10/1991  Nakamura et al.
5,127,726 A  *  7/1992  Moran ...................... 374/237.2
5,208,528 A     5/1993  Quintard
5,246,291 A     9/1993  Lebeau et al.
5,250,809 A  * 10/1993  Nakata et al. .................. 374/5
5,582,485 A  * 12/1996  Lesniak ......................... 374/5
5,984,522 A    11/1999  Koizumi
6,146,014 A  * 11/2000  Bruce et al. ................ 374/161
6,269,719 B1 *  8/2001  Easton et al. .................. 83/54
6,273,603 B1 *  8/2001  Cheindline et al. ........... 374/43
6,360,935 B1 *  3/2002  Flake ......................... 228/103
6,517,236 B2 *  2/2003  Sun et al. ...................... 374/4

* cited by examiner

Primary Examiner—Diego Gutierrez
Assistant Examiner—Yaritza Guadalupe
(74) Attorney, Agent, or Firm—Townsend and Townsend and Crew LLP; Kenneth R. Allen

(57) ABSTRACT

A method for inspecting an object and detecting defects is taught (BGA and Flip-Chip solder joints on a PCB particularly). The method comprises injecting a thermal stimulation on the object; capturing a sequence of consecutive infrared images of the object to record heat diffusion resulting from the heat pulse; comparing the heat diffusion on said object to a reference; and determining whether the object comprises any defects. Also described is a system comprising a mounting for mounting the object; a thermal stimulation module for applying a thermal stimulation to the bottom surface of the object; an infrared camera for capturing infrared images of the object on the top surface of the object to record a change in infrared radiation from the top surface resulting from the thermal stimulation; and a computer for comparing the change in infrared radiation within a region on the top surface to a reference and determining whether the object comprises any defects.

27 Claims, 5 Drawing Sheets

METHOD AND APPARATUS FOR DETECTION OF DEFECTS USING THERMAL STIMULATION

CROSS-REFERENCES TO RELATED APPLICATIONS

The present application claims priority to U.S. provisional application Ser. No. 60/371,971 filed on May 10, 2002, entitled "Method and Apparatus for Detection of Defects Using Localized Thermal Stimulation" and is a continuation in part of U.S. patent application Ser. No. 09/986,712 filed Nov. 9, 2001, entitled "Method and Apparatus for Detection of Defects Using Localized Heat Injection of Narrow Laser Pulse," now pending, the contents of both of which applications are incorporated by reference in their entirety.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK.

Not Applicable

BACKGROUND OF THE INVENTION

The invention relates to the field of industrial inspection. More specifically, it relates to the inspection of the quality and integrity of junctions and connections, such as those for devices mounted on Printed Circuit Boards (PCBs).

It is known that an object such as a populated Printed Circuit Board Assembly (PCBA) may be inspected for defects by a procedure wherein such a PCBA is heated in order to obtain an infrared (IR) image via an IR camera. The captured image is then compared to a standard IR image of a known defect-free populated PCBA in order to evaluate the quality of the connections and junctions on the tested PCBA. What varies in the state of the art is the way the object under inspection is heated.

For example, U.S. Pat. No. 5,052,816 discloses a method and apparatus for junction inspection of electronic parts wherein a plurality of lead wires such as those from an IC (an integrated circuit) are irradiated by a fan beam at the same time. U.S. Pat. No. 5,208,528 discloses a method for inspecting a PCBA, and particularly for inspecting solder joints on the PCBA. This method is characterized by the heating of the PCBA, which is done either by pulsed or brief heating, or in a laminar fashion using a quartz lamp. U.S. Pat. No. 5,246,291 teaches a bond inspection technique for a semiconductor chip wherein a bonding process heats each package lead bonded to each contact area, and an IR camera captures an IR image. A laser can also be used to heat the leads, heating a plurality of leads at once. U.S. Pat. No. 5,984,522 discloses an apparatus for inspecting bump junctions in a semiconductor flip chip mounting wherein the surface of the semiconductor bare chip is irradiated with a laser light and radiation heat from the heated chip is detected with an IR camera.

Since it is essential to detect defects of electronic components such as Ball Grid Arrays (BGAs), Flip Chips, and semi-conductor devices, there is a need to provide an inspection technology, which is relatively easy to use, reliable, and can selectively identify defects due to absence, poor quality or out of tolerance of a solder joint.

BRIEF SUMMARY OF THE INVENTION

According to a first aspect of the present invention, there is provided a method for inspecting an object and detecting defects, the method comprising: injecting a heat pulse by light beam at a selected point on the object; capturing a sequence of consecutive IR images of the object to record heat diffusion over time resulting from the heat pulse; comparing the heat diffusion over time at the point on said object to a reference; and determining whether the object comprises any defects.

The method is adapted to be used for detecting anomalies in solder junctions of ball-grid arrays and flip chips mounted on PCBs. The heat pulse is directed to the bottom surface of the PCB, thereby producing IR emissions at the top surface of the component as the heat is diffused through the PCB and the electronic component. An IR camera captures a sequence of IR images and compares the data to reference data gathered from known defect-free PCBAs.

In one embodiment, an entire sequence of points on a PCBA is programmed into the system and each point is consecutively inspected without human intervention. The PCBA or the area to be inspected is given time to return to ambient temperature in between inspection of each point.

According to a second aspect of the invention, there is provided an apparatus for inspecting an object and detecting defects, the apparatus comprising: a mounting module for mounting the object; a pulsed laser source having a beam able to be positioned for providing a heat pulse at a precise location on the object; an IR camera for capturing IR images of the object; a frame grabber for capturing a sequence of image signals from the IR camera; a memory unit for storing data representative of heat diffusion over time resulting from the heat pulse obtained from the sequence of image signals; and an analyzing unit for comparing the heat diffusion data to a reference data set, said reference comprising upper and lower limits of acceptable thermal heat diffusions of a specific area on the object.

The apparatus includes, in part, an X-Y galvanometer to align the pulsed laser source with the precise location on the object. The apparatus may also include focusing optics to converge, diverge, and deflect the laser beam coming from the pulsed laser source, an optical power attenuator to adjust power of the heat pulse, and an input/output interface to control the X-Y galvanometer, the pulsed laser source, and the optical power attenuator.

In some embodiments, the mounting module further includes register pins to properly fix in space the object under inspection. The mounting module may also include a stage that allows the object to be moved in the x, y and z directions.

According to a third aspect of the present invention, there is provided a method for detecting defects in an object, the method comprising providing a thermal stimulation to a first side; capturing a sequence at least one infrared image of the object on a second side to record a change in IR radiation from the second side resulting from the thermal stimulation; comparing the change in IR radiation within a region on the second side of the object to a reference; and determining whether the object comprises any defects In one embodiment, thermal stimulation is provided by injecting a heat pulse into the object by means of a directed light beam, such beam comprising either coherent light, as from a laser, or incoherent light, as from a flash lamp. The heat pulse is directed to an outer surface of the PCBA (board side or component side) and IR radiation at the second outer surface of the PCBA (component side or PCB side, respectively) is measured by an IR camera that captures a sequence of IR images. A computer processing system compares this data (i.e. IR images) to reference data corresponding to known defect-free PCBAs. When the light beam strikes the first surface of the PCBA, the temperature of the surface increases in response to the heat absorbed from the light beam. The heat introduced at the surface diffuses through the material of the PCB, or component, causing a temperature rise at one side of the solder junction. Heat is conducted through the solder junction to the other side of the solder junction in accordance with the temperature difference created across the junction. The heat continues to diffuse through the material of the component, or PCB, causing a temperature rise at its outer surface where the IR radiation emanating from this surface is recorded by an IR camera. A defect in the solder junction disturbs the normal conduction of heat across the solder junction, which in turn causes an anomalous IR radiation pattern to be observed at the second outer surface.

The method may further include selective heating of a plurality of solder junctions on a PCBA using a collimated laser beam that is focused on a small spot, or point, on the surface of the PCB side of the PCBA in close proximity to the targeted solder junction. The laser beam is selectively stepped across a plurality of solder junctions while ensuring sufficient time for dissipation of heat before a neighboring solder junction is targeted by the laser beam, or heat source.

An entire sequence of points on a PCBA is programmed into the system and each point is consecutively inspected without human intervention. The PCBA or the area to be inspected is given time to return to a non-disturbing level temperature in between inspection of each point.

According to a fourth aspect of the invention, there is provided a method for inspecting like objects by thermal stimulation and imaging comprising the steps of: selecting a plurality of thermal injection locations on said objects; determining a desired thermal injection energy for said locations; determining by observation an area S on at least one of said objects around each of said locations disturbed by thermal diffusion resulting from injections of said desired thermal injection energy and a time T required for dissipation of said desired thermal injection energy to a non-disturbing level, said desired thermal injection energy and said locations resulting in overlap of said area S associated with at least some neighboring ones of said locations; determining from said locations, said area S, and said time T, an injection sequence for injecting said desired thermal injection energy in said objects at said locations while imaging component surface IR radiation, which is affected by diffusion of said desired thermal injection energy through said object without disturbance of thermal diffusion from neighboring one of said locations; using said injection sequence to inspect said object.

In some embodiments, the method further comprises heating of an area of the PCBA surface below the component using a light beam such that heat diffuses through all solder junctions at, or nearly at, the same time thereby providing a simultaneous inspection of all solder junctions. The light beam may be generated by a laser or by a flash lamp. As the heat diffuses throughout the solder junctions, a portion of the heat will be conducted away from the solder junction pad on the PCB via the copper trace connecting said pad to other components on the PCB. This will cause some heating of the copper traces, which will conduct a portion of the heat to the interconnected components and to the surrounding PCB material. The ensuing pattern of heating due to this effect will be characteristic of the PCB design. A specific location, or trace, that indicates a heating anomaly can be directly traced back to the solder junction, which may be defective, thus causing the anomaly. This can be done using the PCB layout data, which may be in Computer Aided Design (CAD) format. IR camera measurements may be made on the PCB side of the PCBA, on the component side of the PCBA, or on both sides of the PCBA, according to the PCBA design.

According to a fifth aspect of the invention, there is provided a system for inspecting an object and detecting defects, the system comprising: a mounting for supporting said object and exposing a top surface and a bottom surface of the object; a thermal stimulation module for applying a thermal stimulation to the bottom surface of the object; an IR camera for capturing IR images of the object on the top surface of the object to record a change in IR radiation from the top surface resulting from the thermal stimulation; and a computer for comparing the change in IR radiation within a region on the top surface to a reference and determining whether the object comprises any defects.

In some embodiments, the computer comprises a frame grabber for capturing a sequence of image signals from the IR camera; a memory unit for storing camera data representative of the component surface heating resulting from the heat pulse obtained from the sequence of image signals; and an analyzing unit for comparing the surface IR radiation data to a reference data set, the reference comprising upper and lower limits of acceptable IR radiation of a specific area on the object. The thermal stimulation module comprises a sequencer module for determining a sequence for applying the thermal stimulation to a plurality of locations on the object such that sufficient time is provided for dissipation of heat at a first location before a neighboring location is thermally stimulated.

In some embodiments, the apparatus also comprises a means to align the pulsed Laser source with the precise location on the object and to control its intensity. This can be achieved with an X-Y galvanometer and an optical power attenuator. Other means are possible. The apparatus can also comprise focusing optics to converge, diverge, and deflect the Laser beam coming from the pulsed Laser source, and an input/output interface to control the X-Y galvanometer, the pulsed Laser source, and the optical power attenuator.

The mounting module comprises register pins to properly fix in space the object under inspection. The mounting module can also comprise a stage that allows the object to be moved in the x, y, and z directions.

It is appreciated that when the specification refers to thermal stimulation, this means injecting or removing heat from the surface to be stimulated in a controlled manner. Injecting heat may be done using a Laser pulse. It can also be done via a flash lamp or via other mechanical contact or non-contact means. Heat can be extracted by mechanical contact of a cold source or instrument at the location to be thermally stimulated. Hot and cold can also be used in combination in order to create a better contrast for the IR camera.

It is also appreciated that more than one location on a PCBA may be thermally stimulated at one time.

It is also appreciated that when the specification refers to IR camera, this means a camera containing a focal plane array that is sensitive to radiation emitted in the IR portion of the spectrum and capable of providing a stream of images to the computer processing system.

BRIEF DESCRIPTION OF THE DRAWINGS

These and other features, aspects and advantages of the present invention will become better understood with regard to the following description and accompanying drawings wherein.

DETAILED DESCRIPTION OF THE INVENTION

While illustrated in the block diagrams as ensembles of discrete components communicating with each other via distinct data signal connections, it will be understood by those skilled in the art that the preferred embodiments are provided by a combination of hardware and software components, with some components being implemented by a given function or operation of a hardware or software system, and many of the data paths illustrated being implemented by data communication within a computer application or operating system. The structure illustrated is thus provided for efficiency of teaching the present preferred embodiment.

Although this detailed description refers mainly to the inspection of defects on PCBAs and between soldered electrical components and the PCB, it can be appreciated that the method taught can be applicable to detect defects of any type of object for which heat diffusion over time can be measured.

Figure 1:
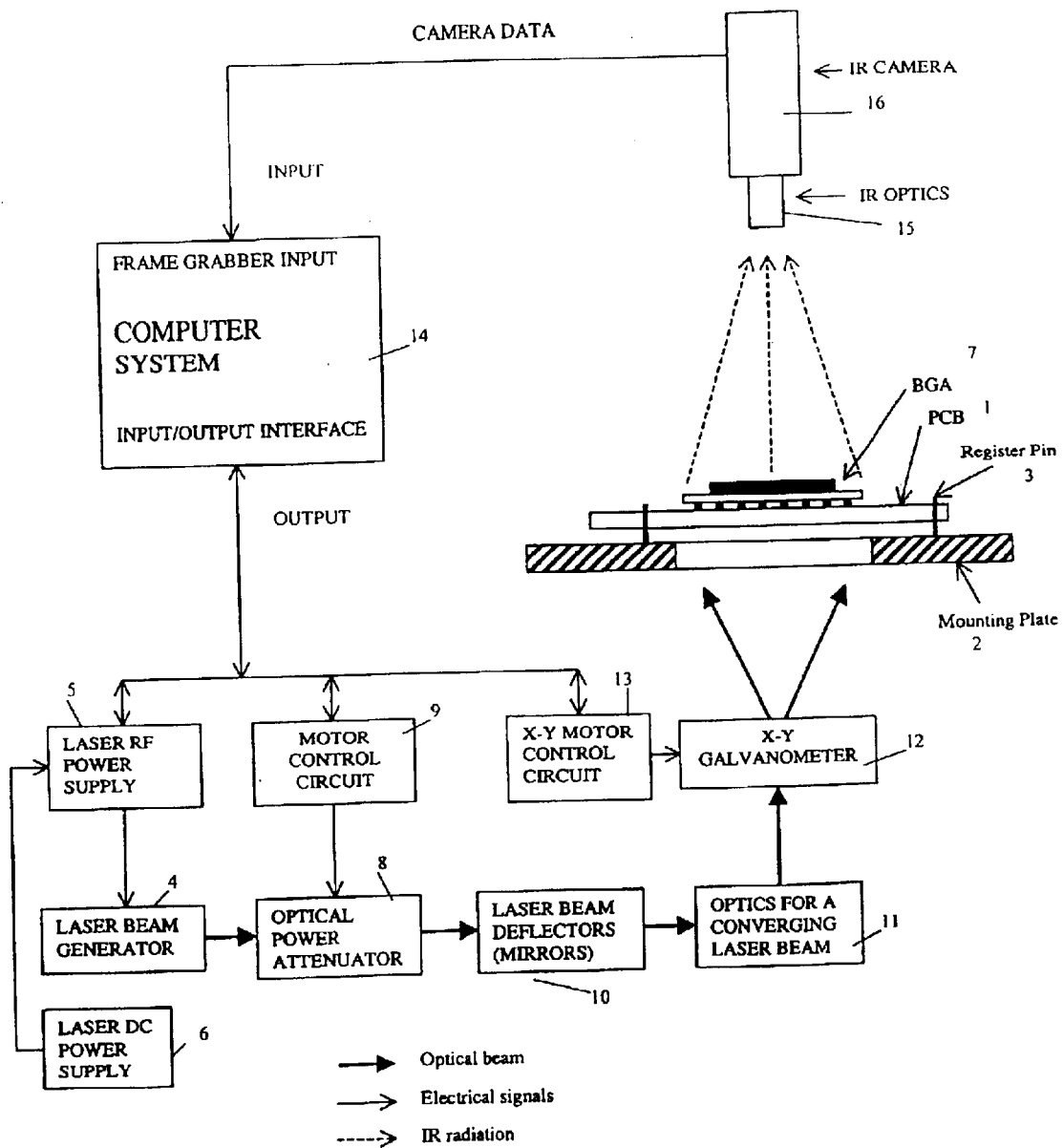
FIG. 1 is a schematic diagram illustrating an embodiment of the present invention.

FIG. 1 illustrates an apparatus for inspecting the quality and integrity of hidden solder junctions and connections of area array devices, such as a BGA and flip-chip, mounted on a PCB. A PCB assembly 1 is mounted on a mounting plate 2. Register pins 3 are used to properly align the PCBA and to ensure a precise positioning in space with respect to the light beam and the IR camera. The junction points of the BGA 7 to the board are hidden and inaccessible visually. A computer system 14 selects a programmed solder junction position by setting the X-Y motor control circuit 13 of the X-Y galvanometer 12. The computer fires the Laser beam generator 4, powered by a Laser Radio Frequency (RF) power supply 5 and a Laser DC power supply 6, supplying an optical beam to an optical power attenuator 8. The attenuator 8 is controlled by the motor control circuit 9 and transmits the optical beam to Laser beam deflectors 10 and optics for a converging beam 11 until the optical beam reaches an X-Y galvanometer 12. The galvanometer 12, controlled by the X-Y control circuit 13, is responsible for directing the optical beam towards a selected area of the mounting plate 2 and selectively heating one or more solder junctions in the BGA 7 through the PCB 1.

Once the heat diffuses through the material and appears at the top surface of the BGA, the IR camera 16 captures an IR image, transforming the IR radiation from the BGA surface into electronic data, and sends it to the computer system 14 to be processed and analyzed. The IR optics 15 are designed to get the maximum spatial resolution for best performance.

This mode of operation, called transmissive mode of operation, differs from a reflective mode of operation, in that the thermal stimulation is applied to a surface on the opposite side of the solder junction under inspection to that of the surface from which the IR measurements are made, thus representing a more direct measure of the heat diffusing through the junction, whereas in the reflective mode of operation, the thermal stimulation is applied to the same surface from which the IR measurements are made, and the cooling of this surface due in part to heat diffusion through the solder junction under inspection is measured, representing a more indirect measure of the heat diffusing through the junction. The direct measurement of the transmissive mode provides a more robust measurement approach.

More specifically, in the transmissive mode, the heat that is injected at the bottom surface of the PCB diffuses throughout the PCB material, including its copper layers and traces, to the base of the solder junction. The temperature differential created between the solder junction interface and the top surface of the component causes the heat to diffuse through the encapsulation of the component to said top surface. The corresponding heat radiated from the top surface is detected by the IR camera, thus presenting a direct measurement of the heat diffused through the solder junction, which will be disturbed by the presence of an anomaly.

The main parts of the computer system 14, which are not explicitly shown in the figure, are a frame grabber to read the analog or digital data from the IR camera 16 and to format it in a manner such that it can be stored and later processed in the PC computer, an input/output Interface to control the Laser Pulses, the programmable optical power attenuator 8 and the X-Y galvanometer scanner 12 positions, and an application software to compare the measured IR radiation pattern from the surface of the device under test with a stored reference on a camera pixel by pixel basis at the lowest level. Various image processing criteria can be used to compare the test signal to a reference signal to identify statistical anomalies, such as dual threshold statistical acceptance criteria, min-max acceptance criteria or other means to accept/reject a pixel or a pattern. Comparison between the two IR patterns is performed by the computer system 14. The computer system 14 captures and stores the specified sequence of images in the PC with the proper synchronization. The computer system 14 then selects the next solder junction position to be inspected and the process is repeated. When all of the specified solder junctions have been tested, the area array device, or BGA, capture sequence and storage is completed and the computer processes all of the specified solder junctions and outputs a complete result for the entire area array device, or BGA, under inspection.

In one embodiment, a $CO_2$ laser is used to deliver pulses of duration less than one second at a power level that maximizes thermal stimulation without causing thermal damage to the article under test, and with the laser energy concentrated on a spot size on the order of a solder junction diameter at the nominal solder junction location. The IR camera 16 captures consecutive images at a standard video rate of 30 frames per second, although other rates are possible, for a duration dependent upon the time required for the heat to diffuse through the PCB/component assembly. The Laser pulse is synchronized with the frame timing of the camera. An alternate type of Laser, such as YAG or a Laser diode, can be used to provide the required thermal stimulation to the PCB.

Alternatively, in this embodiment, instead of using an X-Y galvanometer to direct the Laser beam to the test point on the PCBA, the Laser can be fixed and the mounting plate moved. The mounting plate, with the PCBA in a fixed position on it, can move in the x, y and z position in order to properly align the PCBA and the Laser. Other means are possible such that the necessary alignment of the thermal stimulation source to the desired proximity of the solder junctions under test, or point on the PCB surface, is achieved in a selectable and repeatable manner.

Figure 2:
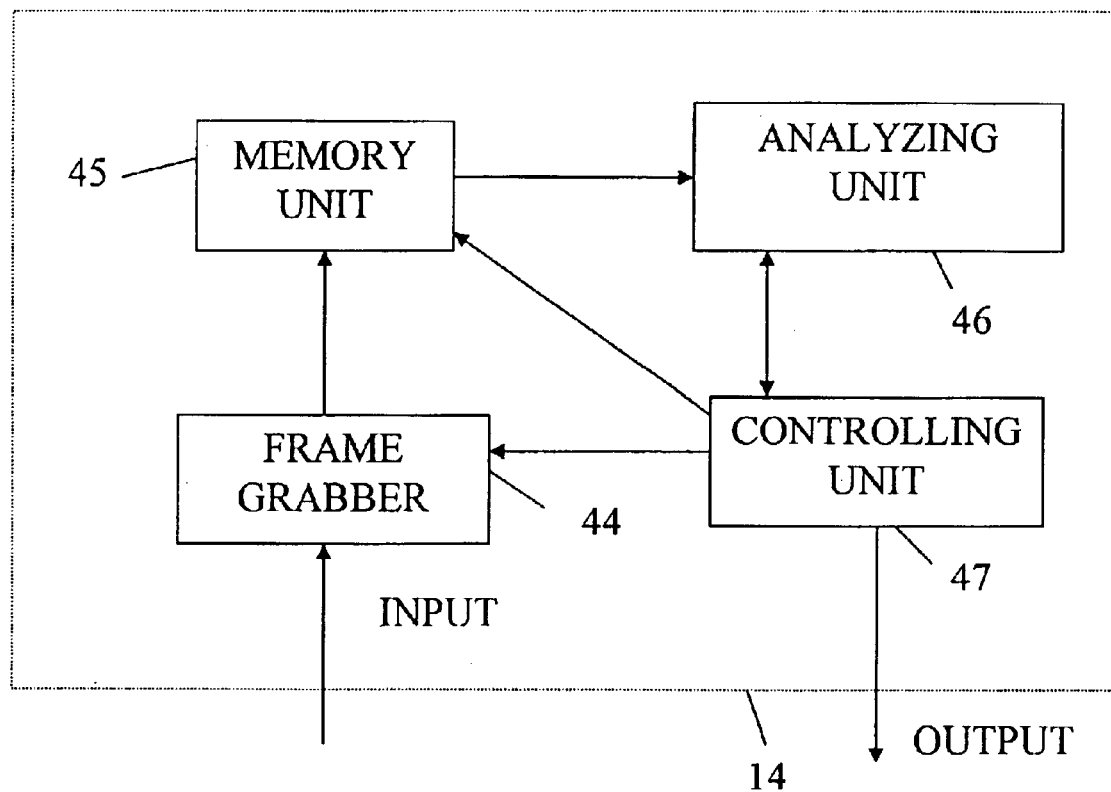
FIG. 2 is a block diagram of the Computer system controlling the apparatus.

FIG. 2 is a block diagram representing module 14 of FIG. 1. A frame grabber 44 captures a sequence of image signals from the IR camera 43 at specific points in time after the application of the thermal stimulation to the PCBA by the pulsed Laser source 41. A memory module 45 stores data representative of the component surface heating over time resulting from the thermal stimulation and obtained from the sequence of image signals. This information is then passed on to an analyzing module 46 to compare the component surface heating data to a reference data set. The reference data set comprises upper and lower limits of acceptable IR radiation for a specific area on the PCBA (e.g. a pixel) and at a specific point in time following the application of the laser pulse. This reference data set is derived from an analysis of data collected from a statistically significant number of known defect-free PCBAs. A controlling unit 47 controls all other modules within the computer system 14. It also controls the X-Y galvanometer 12, the Laser beam generator 4, and the optical power attenuator 8 (optional). The controlling module 47 contains a programmed sequence of points to which it directs the Laser beam in a sequential manner.

Figure 3:
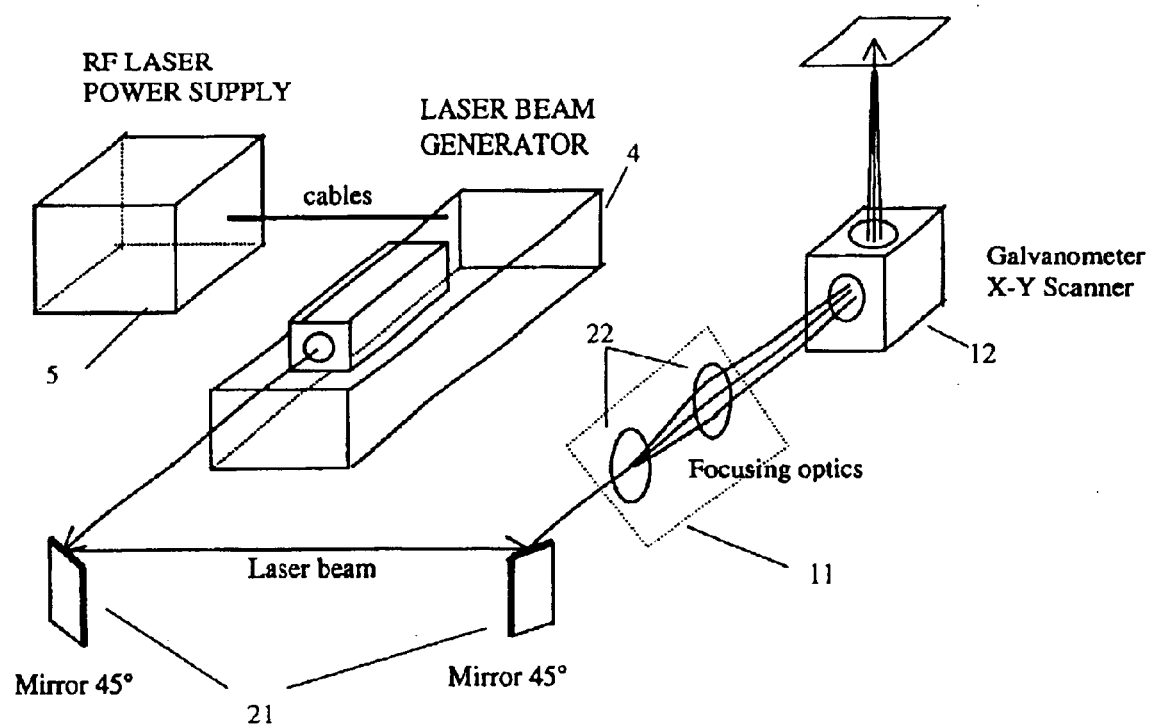
FIG. 3 is a schematic diagram illustrating an embodiment of the LASER unit.

FIG. 3 is a description of the Laser unit used in the apparatus of the embodiment. The RF Laser power supply 5 and the Laser beam generator 4 are connected by electrical cables. The Laser beam generator 4 generates sufficient optical power so as to induce a hot spot on the bottom surface of the PCB. A $CO_2$ Laser has been used in the apparatus of the embodiment. The Laser beam deflector unit 10 comprises two small, flat mirrors 21, each angled so as to reflect the beam towards the optics for a converging Laser beam 11. The optics for a converging Laser beam 11 comprises several lenses 22 used to focus and collimate the beam before directing it into the X-Y galvanometer scanner 12. The X-Y galvanometer scanner 12 comprises of two orthogonal flat mirrors mounted on two motor axis (not shown). The two motors are positioned by the computer through proper electronic/electrical interfaces. The Laser beam spot size is adjustable. The laser beam irradiates the area under the location of the solder junction under inspection. When this area has been heated by the laser pulse, the X-Y galvanometer scanner 12 directs the laser beam to the next solder junction to be inspected according to the predetermined sequence and the Laser is fired again for the same period of time. The RF Laser power supply 5 provides the RF energy to stimulate the $CO_2$ Laser, which emits the light beam during the time that the RF energy is present. When the RF energy is absent, the Laser stops lasing immediately. The RF Laser power supply 5 monitors and controls the pulse duration and repetition rate according to electronic signals received from the computer input/output interface.

One embodiment of the present invention requires calibration prior to PCBA testing and analysis. A calibration is carried out to determine and store in computer memory various system parameter settings (i.e. intensity, shape, duration, repetition rate, etc.) for each specific article under test, and to generate a corresponding data reference set. The reference data set, which describes the acceptable range of variation of the IR radiation, is derived from the mean and standard deviation calculations on a pixel by pixel basis for each frame of a sequence of IR images recorded for a statistically significant number of known defect free samples. The upper and lower limits of the acceptance range are calculated for each pixel and stored as the reference standard to which all tested PCBAs are compared.

It is important that the thermal stimulation applied to the PCBA be well known. This can be achieved using a stable and repeatable Laser source to provide the thermal stimulation. Further, when an IR test image is compared with the reference data set they must both correspond to the same instant in time following application of the thermal stimulation. Thus, the apparatus ensures reproducibility of spatial positioning of the test article in space (x, y planar coordinates), intensity of thermal stimulation (laser pulse intensity) and temporal synchronization (comparison of test and reference images at the same instance in time following thermal stimulation).

Figure 4:
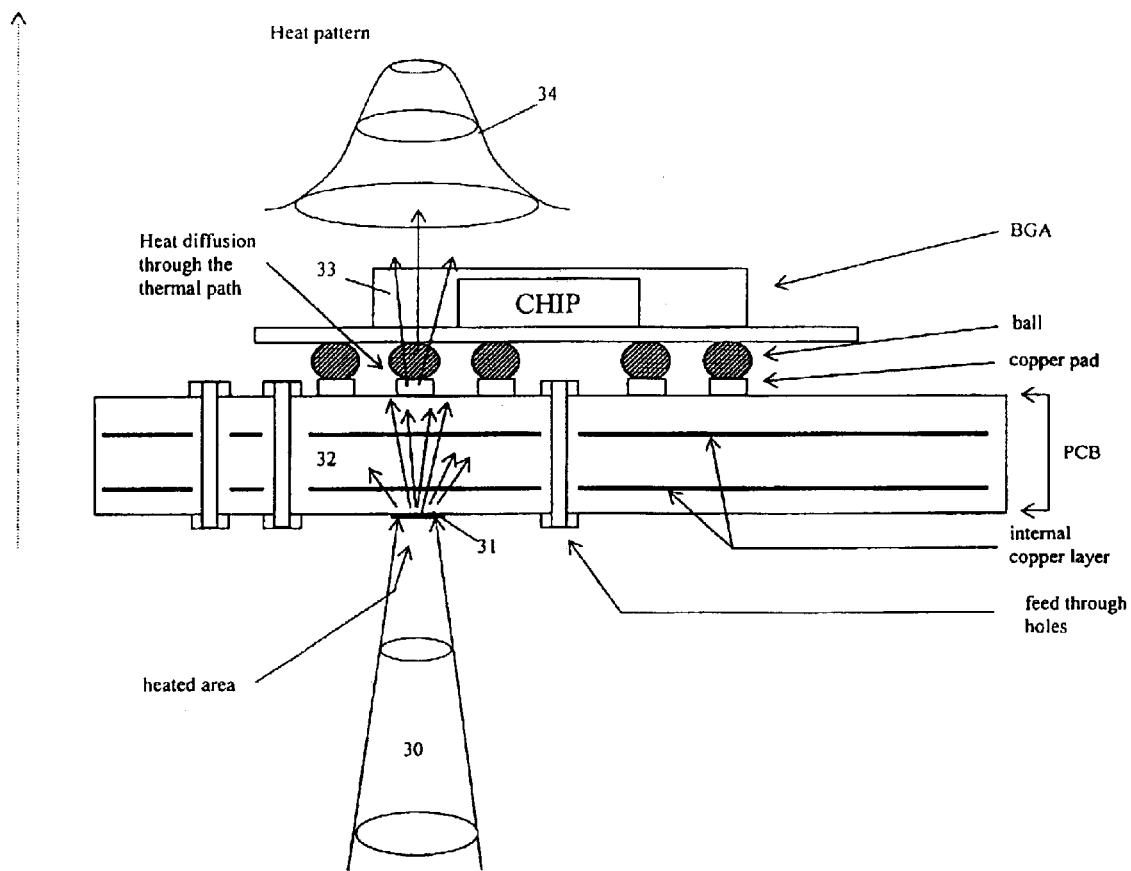
FIG. 4 is a schematic diagram illustrating heating a solder joint.

FIG. 4 is a close-up schematic of the thermal stimulation of a solder junction of an area array device (BGA) and the heat diffusion from the surface of the PCB to the top surface of the BGA component. A light beam 30 is positioned under a solder junction of a ball-grid array. The Laser light pulse heats the small area 31. Heat diffuses through the materials 32 and appears at the BGA top surface 33. A radiation pattern 34 is then recorded by an IR camera. From the drawing, the junction point between the solder junction (solder ball) and the PCB is clear.

When a specific solder junction is inspected by application of a thermal stimulation in close proximity to the solder junction, a portion of the heat that is injected can diffuse into the area of a nearest neighbor solder junction, thereby disturbing it from its normal ambient condition. Further, if the nearest neighbor solder junction is to be inspected next, a waiting period may be required for it to return to its undisturbed condition prior to its thermal stimulation, resulting in longer inspection times. Reductions in inspection time can be achieved by next thermally stimulating a non-neighbor solder junction that is located a sufficient distance away from the previously thermally stimulated solder junction such that it is not disturbed by the previous thermal stimulation, and to return to the nearest neighbor after a sufficient period of time T has passed to allow the nearest neighbor to return to its undisturbed condition. An aspect of the embodiment is the design of a unique sequencer to determine an optimum sequence by which to thermally stimulate the entire array of solder junctions of the area array device, thereby avoiding the aforesaid condition. A processing algorithm provides a chronological sequence for thermally stimulating solder junctions according to the following criteria: (1) there must be no significant thermal disturbance of a solder junction from ambient conditions caused by the thermal stimulation of another solder junction, and (2) the time required for thermally stimulating all of the solder junctions contained in one array is minimized. Thus, the function of the sequencer is to provide the means to selectively heat all solder joints in an automatic fashion in the shortest time possible, while ensuring sufficient time is provided for dissipation of heat before a neighboring solder junction is thermally stimulated.

The sequencer controls the stepping of the X-Y galvanometer 12. Because the X-Y galvanometer, controlled by the X-Y control circuit 13, directs the optical beam at a selected area of the mounting plate 2, the X-Y control circuit 13 provides the galvanometer with the coordinates of the next solder junction to thermally stimulate, according to the predetermined sequence. The sequencer program contained within the computer system 14 computes the optimum sequence automatically according to a unique algorithm. Alternatively the laser firing sequence can be determined manually or external to the system and entered via the input/output interface.

The sequencer algorithm operates according to a specified set of rules. When a solder junction is thermally stimulated by the Laser, the heat diffuses into the surrounding area, dissipating in the process. An optimum trade-off of spatial and time constraints determined by the sequencing algorithm provides the surrounding area sufficient time to dissipate the heat such that it does not interfere with a subsequent injection of heat. The spatial and temporal trade variables are defined as follows: (1) an area surrounding the solder junction that is being thermally stimulated (S), and (2) the time needed for the heat generated by the thermal stimulation to sufficiently dissipate (T) within this area so as to be considered insignificant, or non-disturbing, and thus would not adversely affect the inspection of neighboring balls. T and S are a function of the energy of the thermal pulse and the heat transport properties of the populated PCBA.

The sequencing algorithm determines a solution for the inspection of all solder junctions in the shortest possible time, according to the following constraint: no solder junction can be thermally stimulated if it exists in the surrounding area of a previously thermally stimulated solder junction until a period of time T has elapsed. The system uses different scanning strategies to find the best solution. Values of S and T are selected to ensure no thermal disturbances between thermally stimulated junctions. If no solution exists for the selected values of S and T, the algorithm adds 'dead time' between laser firings. This can be thought of as thermally stimulating a number of 'virtual' solder junctions. Additionally, the algorithm can be adapted to adjust the values of S and T in order to find an acceptable solution.

Figure 5:
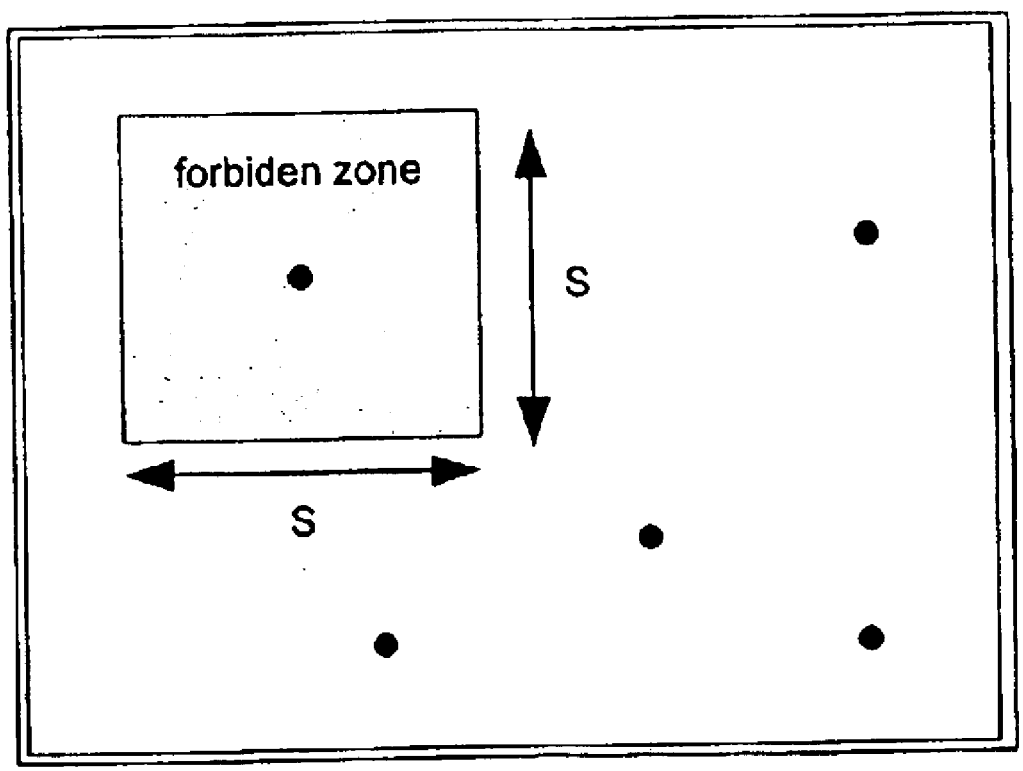
FIG. 5 is a schematic diagram illustrating the surrounding area of a solder ball.

FIG. 5 illustrates an example area (S) in which the algorithm restricts thermal stimulation of solder junctions for a time period T after the solder junction in the center of the area has been thermally stimulated.

Alternatively, the sequencer can be used to control the sequencing of active thermal testing of a number of different components on a PCBA. The values of S and T can be unique for each component, due to physical differences in the components that can result in different heat transport properties. The components can be distributed on the PCBA in any manner, so long as the sequencer knows the coordinates of each component and can input them to the X-Y motor control circuit. Further, the injected energy can be unique for each component. Different components can demand different degrees of thermal stimulation and different PCBs can have different damage threshold levels.

Further reductions in inspection time are possible, albeit at a cost of increased system complexity, by thermally stimulating and imaging two locations simultaneously. In this case, two sequences are used that can work together to ensure that there is no interference between thermal stimulation and IR imaging. Alternatively, a sequence can comprise subsequences, or sets, of locations whose areas S do not overlap within their subsequence, but that the overlap is between subsequences. Each subsequence can be executed simultaneously and the sequencer can strategically execute subsequences so as to not interfere with each other.

Another feature of the invention is a processing algorithm that combines the results of each solder junction inspection in a manner so as to present to the operator a single integrated representation of the inspection results for the complete area array device containing all solder junctions. Accordingly, the apparatus secures the article under test in place, ensuring a precise positioning in space, maintains the PCBA at a stable temperature, programs a complete set of points on the PCBA to be thermally stimulated, injects a heat pulse by laser beam at a next point on the PCBA, the next point being determined by the set of points, repeats the step of injecting a heat pulse by light beam at a next point until all points in the entire set of points have been inspected, and provides a compilation of results to produce a complete analysis after the entire set of points on the PCBA has been inspected. The step of programming an entire set of points on the PCBA to be inspected can be done using the sequencer or manually. The set of points may comprise all of the components on the PCBA, or only a portion of them.

It will be appreciated that various modalities of applying thermal stimulation to the surface of a PCB assembly, various modalities of processing the detected IR radiation data to identify anomalies also apply and that various mechanical variants optimized for in-line production screening or off-line diagnostics and failure analysis are also feasible in combination with the methods and apparatus discussed herein.

It will be understood that numerous modifications thereto will appear to those skilled in the art. Accordingly, the above description and accompanying drawings should be taken as illustrative of the invention and not in a limiting sense. It will further be understood that it is intended to cover any variations, uses, or adaptations of the invention following, in general, the principles of the invention and including such departures from the present disclosure as come within known or customary practice within the art to which the invention pertains and as may be applied to the essential features herein before set forth, and as follows in the scope of the appended claims.

What is claimed is:

1. A method for inspecting and detecting defects in an object, said method comprising:
   providing a thermal stimulation to a first side of said object;
   capturing at least one infrared image of said object on a second side to record a change in infrared radiation from said second side resulting from said thermal stimulation;
   comparing said change in infrared radiation within a region on said second side of said object to a reference; and
   determining whether said object comprises any defects, wherein said providing a thermal stimulation comprises:
   using a focused laser beam to inject heat on a point in close proximity to said solder junctions;
   selecting a desired thermal stimulation energy for each of said at least one point on said object;
   selectively stepping said focused laser beam across said solder junctions while ensuring sufficient time for dissipation of heat before a neighboring solder junction is thermally stimulated;
   determining an area S on at least one of said objects around each of said locations disturbed by thermal propagation resulting from injections of said desired thermal injection energy and a time T required for dissipation of said desired thermal injection energy to a non-disturbing level, said desired thermal injection energy and said locations resulting in overlap of said area S associated with at least some neighboring ones of said locations; and
   determining from said locations, said area S, and said time T, an injection sequence for injecting said desired thermal injection energy in said objects at said locations while imaging thermal propagation of said desired thermal injection energy in said object without disturbance of thermal propagation from neighboring one of said locations.

2. A method as claimed in claim 1, wherein said capturing at least one infrared image comprises capturing a sequence of consecutive images over time.

3. A method as claimed in claim 2, wherein said comparing said change comprises comparing said change in infrared radiation over time to a reference.

4. A method as claimed in claim 1, wherein said object is a printed circuit board assembly and said detecting defects comprises detecting anomalies in solder junctions of area array devices on said printed circuit board assembly.

5. A method as claimed in claim 4, wherein said first side is a bottom surface of said printed circuit board assembly and said second side is a top surface of a component assembled to said printed circuit board assembly.

6. A method as claimed in claim 1, wherein said providing thermal stimulation comprises selecting at least one point on said object and injecting a localized, narrow, heat pulse at said point.

7. A method as claimed in claim 1, wherein said providing a thermal stimulation comprises injecting heat using a flash lamp.

8. A method as claimed in claim 1, wherein said thermal stimulation comprises removing heat by injecting cold.

9. A method as claimed in claim 1, wherein said capturing a sequence of consecutive infrared images comprises measuring emitted infrared radiation using an infrared camera composed of a focal plane array.

10. A method as claimed in claim 1, wherein said providing a thermal stimulation comprises thermally stimulating more than one location at one time.

11. A method as claimed in claim 1, wherein said providing a thermal stimulation comprises providing said thermal stimulation to a localized area of said object, and upon detection of an anomaly at a point within said area, a localized heat pulse is applied to said point to confirm said detection of an anomaly.

12. A method for inspecting like objects by thermal stimulation and imaging comprising the steps of:
   selecting a plurality of thermal injection locations on said objects;
   determining a desired thermal injection energy for said locations;
   determining an area S on at least one of said objects around each of said locations disturbed by thermal propagation resulting from injections of said desired thermal injection energy and a time T required for dissipation of said desired thermal injection energy to a non-disturbing level, said desired thermal injection energy and said locations resulting in overlap of said area S associated with at least some neighboring ones of said locations;
   determining from said locations, said area S, and said time T, an injection sequence for injecting said desired thermal injection energy in said objects at said locations while imaging thermal propagation of said desired thermal injection energy in said object without disturbance of thermal propagation from neighboring one of said locations; and
   using said injection sequence to inspect said object.

13. A method as claimed in claim 12, wherein said like objects are solder junctions of area array devices on a printed circuit board assembly.

14. A method as claimed in claim 13, wherein said using said injection sequence to inspect said object comprises providing a thermal stimulation according to said sequence.

15. A method as claimed in claim 14, wherein said providing thermal stimulation comprises injecting heat using a coherent external light source.

16. A method as claimed in claim 14, wherein said thermal stimulation comprises removing heat by injecting cold.

17. A method as claimed in claim 14, wherein said providing a thermal stimulation comprises using a focused laser beam to inject heat on a point in close proximity to said solder junctions.

18. A method as claimed in claim 14, wherein said providing a thermal stimulation comprises thermally stimulating more than one location at one time.

19. A method as claimed in claim 13, wherein said providing a thermal stimulation comprises injecting heat using a flash lamp.

20. A system for inspecting and detecting defects in an object, said system comprising:
   a mounting module for supporting said object and exposing a top surface and a bottom surface of said object;
   a thermal stimulation module for applying a thermal stimulation to said bottom surface of said object;
   an infrared camera for capturing infrared images of said object on said top surface of said object to record a change in infrared radiation from said top surface resulting from said thermal stimulation; and
   a computer for comparing said change in infrared radiation within a region on said top surface to a reference and determining whether said object comprises any defects, wherein said thermal stimulation module comprises a sequencer module for determining a sequence for applying said thermal stimulation to a plurality of locations on said object such that sufficient time is provided for dissipation of heat at a first location before a neighboring location is thermally stimulated; wherein said sequencer module determines an area S on at least one of said objects around each of said locations disturbed by thermal propagation resulting from injections of said desired thermal injection energy and a time T required for dissipation of said desired thermal injection energy to a non-disturbing level, said desired thermal injection energy and said locations resulting in overlap of said area S associated with at least some neighboring ones of said locations.

21. A system as claimed in claim 20, wherein said object is a printed circuit board assembly and said detecting defects comprises detecting anomalies in solder junctions of area array devices on said printed circuit board assembly.

22. A system as claimed in claim 20, wherein said first side is a bottom surface of said printed circuit board assembly and said second side is a top surface of a component assembled to said printed circuit board assembly.

23. A system as claimed in claim 20, wherein said computer comprises:
   a frame grabber for receiving camera data from said infrared camera;
   a memory unit for storing said camera data;
   an analyzing unit for comparing said camera data to a reference; and
   a controlling unit for controlling said frame grabber, said memory unit, and said analyzing unit.

24. A system as claimed in claim 20, wherein said mounting comprises pins for aligning said object with said thermal stimulation module.

25. A system as claimed in claim 20, wherein said thermal stimulation module comprises an X-Y galvanometer for directing said thermal stimulation towards a selected area of said bottom surface of said object.

26. A system as claimed in claim 25, wherein said X-Y galvanometer is controlled by said sequencer module.

27. A system as claimed in claim 20, wherein said thermal stimulation module comprises aligning and converging optics to converge and align a laser beam.

* * * * *